United States Patent
Van Kesteren et al.

(10) Patent No.: US 9,763,600 B2
(45) Date of Patent: Sep. 19, 2017

(54) NITRIC OXIDE MEASUREMENT METHOD AND APPARATUS

(75) Inventors: Hans Willem Van Kesteren, Eindhoven (NL); Teunis Johannes Vink, Eindhoven (NL)

(73) Assignee: KONINKLIJKE PHILIPS N.V., Eindhoven (NL)

( * ) Notice: Subject to any disclaimer, the term of this patent is extended or adjusted under 35 U.S.C. 154(b) by 1075 days.

(21) Appl. No.: 13/577,965

(22) PCT Filed: Feb. 10, 2011

(86) PCT No.: PCT/IB2011/050566
§ 371 (c)(1),
(2), (4) Date: Aug. 9, 2012

(87) PCT Pub. No.: WO2011/101776
PCT Pub. Date: Aug. 25, 2011

(65) Prior Publication Data
US 2012/0310104 A1 Dec. 6, 2012

(30) Foreign Application Priority Data
Feb. 17, 2010 (EP) ..................................... 10153795

(51) Int. Cl.
*A61B 5/083* (2006.01)
*A61B 5/08* (2006.01)

(52) U.S. Cl.
CPC .............. *A61B 5/083* (2013.01); *A61B 5/082* (2013.01)

(58) Field of Classification Search
None
See application file for complete search history.

(56) References Cited

U.S. PATENT DOCUMENTS

| 6,866,637 B2 | 3/2005 | George |
| 2003/0208131 A1 | 11/2003 | George |
| 2003/0229290 A1 | 12/2003 | George et al. |

(Continued)

FOREIGN PATENT DOCUMENTS

| WO | 2009001275 A1 | 12/2008 |
| WO | 2011013046 A1 | 2/2011 |

OTHER PUBLICATIONS

Miller-Keane Encyclopedia and Dictionary of Medicine, Nursing and Allied Health, Apr. 2003, Elsevier Health Sciences, 7th Edition.*

(Continued)

*Primary Examiner* — Jacqueline Cheng
*Assistant Examiner* — Jairo Portillo
(74) *Attorney, Agent, or Firm* — Michael W. Haas

(57) ABSTRACT

There is provided a method of determining at least one parameter value relating to nitric oxide, NO, production in the lower respiratory tract of a subject, the method comprising obtaining a plurality of measurements of NO levels in exhaled air and air flow rate during multiple exhalations of a subject performing tidal breathing; analyzing the plurality of measurements to identify exhalations where the NO produced in the lower respiratory tract dominates the NO contribution from other sources; determining at least one parameter value relating to NO in the lower respiratory tract of the subject from the measurements of NO levels and/or air flow rate obtained during the identified exhalations.

12 Claims, 6 Drawing Sheets

(56) References Cited

U.S. PATENT DOCUMENTS

2007/0048180 A1* 3/2007 Gabriel et al. .................. 422/57
2007/0149891 A1 6/2007 George et al.
2007/0282214 A1 12/2007 George et al.
2009/0247891 A1 10/2009 Wood
2012/0110361 A1 5/2012 Durand et al.

OTHER PUBLICATIONS

P. Condorelli et al., "Characterizing Airway and Alveolar Nitric Oxide Exchange During Tidal Breathing Using a Three-Compartment Model", J. Appl Physiol 96:, Jan. 16, 2004, pp. 1832-1842.
ATS/ERS Recommendations for Standardized Procedures for the Online and Offline Measurement of Exhaled Lower Respiratory Nitric Oxide and Nasal Nitric Oxide 2005:, Am. J. Respir. Crit. Care Med. vol. 171, pp. 912-930, 2005.
Tsoukias, N. M. et al., "A Two-Compartment Model of Pulmonary Nitric Oxide Exchange Dynamics", J. Appl. Physiol. vol. 85, pp. 653-666, 1998.

* cited by examiner a)

b)

a)

b)

NITRIC OXIDE MEASUREMENT METHOD AND APPARATUS

TECHNICAL FIELD OF THE INVENTION

The invention relates to a method and apparatus that measures nitric oxide (NO) in exhaled air, and in particular to a method and apparatus that measures nitric oxide (NO) in air exhaled by a subject performing a tidal breathing manoeuvre.

BACKGROUND TO THE INVENTION

Exhaled nitric oxide (eNO) is a non-invasive marker for airway inflammation. Inflammation of the airways is present in patients with asthma, who produce elevated levels of NO in the lower respiratory tract (bronchi and alveolar part). Therefore, high values of eNO can be used in combination with other pulmonary tests for diagnosing asthma. Furthermore, eNO can be used for monitoring the effectiveness of inhaled corticosteroids (ICS) and in anti-inflammatory asthma management to titrate ICS dosage.

The standardized method of measuring eNO involves the subject participating in a single exhalation experiment in which they breathe out at a fixed flow rate of 50 ml/s and an overpressure of at least 5 cm $H_2O$. Recommendations on a standardized method by the American Thoracic Society and European Respiratory Society are set out in the paper "ATS/ERS Recommendations for Standardized Procedures for the Online and Offline Measurement of Exhaled Lower Respiratory Nitric Oxide and Nasal Nitric Oxide, 2005" American Journal of Respiratory and Critical Care Medicine Vol. 171, pp 912-930 2005.

An exemplary apparatus for performing a fixed flow rate measurement is shown in FIG. 1. The apparatus 2 comprises a tube 3 arranged in a generally 'Y' shape with the three ends forming an air inlet 4, an air outlet 6 and a mouthpiece 8 respectively. A first one-way valve 10 is provided in the tube 3 between the air inlet 4 and the mouthpiece 8 and a second one-way valve 12 is provided in the tube 3 between the mouthpiece 8 and the air outlet 6. The one-way valves 10, 12 are configured so that air is drawn through the tube 3 via the air inlet 4 and mouthpiece 8 when the subject inhales, and air is passed through the tube 3 via the mouthpiece 8 and air outlet 6 when the subject exhales.

The apparatus 2 also comprises a sensor 14 for measuring levels of NO in the exhaled air that is connected to a side stream 15 located between the second one-way valve 12 and the air outlet 6, and a pressure sensor 16 connected to a side stream 17 that is also located between the second one-way valve 12 and the air outlet 6. The pressure sensor 16 measures the pressure resulting from the exhalation of air through a flow restrictor 20 and provides audio and/or visual feedback to the subject on whether the flow and pressure of the exhaled air is appropriate for the measurement (i.e. a fixed flow rate of 50 ml/s and a pressure of at least 5 cm $H_2O$) via a feedback device 18. A processor 19 is connected to the sensor 14 for processing the NO measurements to determine the NO level in the, or a portion of the, exhaled air.

The flow restrictor 20 is provided in the air outlet 6 to make it easier for the subject to reach the required flow and overpressure. Once the required pressure is achieved, the velum—the soft palate consisting of muscle fibers sheathed in mucous membrane responsible for closing off the nasal passages during the act of swallowing and sneezing—is closed preventing NO from the nasal cavity of the subject passing into the oral cavity.

A NO filter 22 can be provided in the tube 3 between the air inlet 4 and the first one-way valve 10 that removes NO from the air drawn into the apparatus 2 from the surrounding environment when the subject inhales.

However, a problem with this apparatus is that it requires a constant exhalation flow for a given period of at least 10 seconds, and this is not simple to perform, in particular for young children, older subjects, or subjects having difficulty breathing. Although commercial systems are available based on the apparatus shown in FIG. 1 that have received approval from the US Food and Drug Administration (FDA) for standardized eNO measurements on children aged 7-18 years and adults under supervision of a trained operator in a physician's office, there is currently no FDA-approved system for use in young children.

Techniques exist to measure an eNO value during oral tidal breathing by the subject. Tidal breathing is a much more straightforward and natural breathing process and thus is much simpler for the subject to perform than tests using single breath exhalations at a fixed flow or tests requiring a breath hold for a certain time. A tidal breathing manoeuvre can be performed by the subjects themselves without guidance and probably in cooperative children from the age of three onwards. Tidal breathing generally involves a breathing frequency of 4-20 breaths per minute for adults and 20-40 breaths per minute for children and exhaled volumes of 300-1000 ml per breath for adults and 100-500 ml for children.

However, a problem with tidal eNO measurement methods is that the increased flow rates (typically 100-500 ml/s) involved reduces the concentration of nitric oxide (NO) in the air at the sensor, which makes the measurement more sensitive to various disturbances like contamination from NO in the environment or NO from the nasal area of the subject.

This problem is related to two issues. Firstly, the standardized fixed flow rate manoeuvre starts with a deep inhalation while tidal breathing involves a shallower inhalation. This means that only some of the air from previous inhalations is exchanged in tidal breathing. Furthermore, during the shorter time involved in a tidal breathing cycle, the NO in the inhaled air is only partly removed by the alveoli in the subject's lungs. Therefore, even when NO-free air is inhaled through the mouth in a tidal breathing manoeuvre, some inhaled nasal NO can "contaminate" the exhaled air.

Secondly, during the exhalation in the standardized fixed flow rate manoeuvre, the velum is closed due to the overpressure, so no NO from the nasal cavity can pass into the oral cavity. However, during tidal exhalation the velum might be open and NO from the nasal cavity can diffuse into the air exhaled through the mouth.

Therefore, there is a need for a method and apparatus that measures NO in exhaled air during a tidal breathing manoeuvre in which at least some of the above mentioned disadvantages are mitigated.

SUMMARY OF THE INVENTION

It has been found that in measurements of nitric oxide (NO) during tidal breathing over multiple breathing cycles, some exhalations provide an accurate determination of the NO produced in the lower respiratory tract, while other exhalations provide an inaccurate value. The invention provides that in a tidal breathing manoeuvre involving multiple breaths, a selection is made of those exhalations or parts of the exhalations where the NO produced in the lower respiratory tract dominates the NO measurement contribution from other sources, such as the environment or nasal cavity of the subject.

Therefore, according to a first aspect of the invention there is provided a method of determining at least one parameter value relating to nitric oxide, NO, production in the lower respiratory tract of a subject, the method comprising obtaining a plurality of measurements of NO levels in exhaled air and air flow rate during multiple exhalations of a subject performing tidal breathing; analyzing the plurality of measurements to identify exhalations where the NO produced in the lower respiratory tract dominates the NO contribution from other sources; and determining at least one parameter value relating to NO in the lower respiratory tract of the subject from the measurements of NO levels and/or air flow rate obtained during the identified exhalations.

In a preferred embodiment, the step of analyzing and/or step of determining comprises using a model describing the flow dependence of NO levels in exhaled air and wherein the at least one parameter relating to NO in the lower respiratory tract is a flow independent parameter of the model. In an alternative embodiment, the step of analyzing comprises using a model describing the flow dependence of NO levels in exhaled air and wherein a single flow independent parameter is used relating to NO in the lower respiratory tract. The NO produced in the lower respiratory tract has a specific flow dependence which is disrupted when NO from other sources is present, so the use of a model describing this flow dependence allows exhalations where the NO produced in the lower respiratory tract dominates the NO contribution from other sources to be identified.

The model in the above embodiments preferably comprises a two-compartment model, a three-compartment model or a trumpet model.

In the embodiment in which the model is a two-compartment model, the exhaled NO, $C_E$, is given by $$C_E = C_w \cdot \left(1 - e^{-D_{aw}/\dot{V}}\right) + C_{alv} \cdot e^{-D_{aw}/\dot{V}}$$

where $C_{alv}$ is the alveolar concentration, $D_{aw}$ is the airway diffusion coefficient, $\dot{V}$ is the air flow rate, the ratio of $C_{alv}/C_w$ and the value of $D_{aw}$ are set to constant values. The wall concentration, $C_w$, can then be determined from the measurements of the NO level and air flow rate. The model can be used for tidal breathing regimes as it is valid for all relevant flow rates, i.e. from above a tidal breathing regime to below 50 ml/s. The use of this model is particularly advantageous during the step of analyzing.

Preferably, in this embodiment, the ratio of $C_{alv}/C_w$ and $D_{aw}$ in the model are set to respective constant values based on a population value or a previous personal value for the subject.

In a preferred embodiment in which the model is a trumpet model, the exhaled NO, $C_E$, is given by $$C_E = \frac{J_{aw}}{\dot{V}}\left(1 + \frac{c_3 \cdot D_{ax}}{\dot{V}}\right)^{-c_4}$$

where $\dot{V}$ denotes the air flow rate, $D_{ax}$ the axial diffusion constant for Nitric Oxide, and $c_3$ and $c_4$ are positive constants. Furthermore, the step of analyzing comprises determining values for the maximum airway wall NO flux, $J_{aw}$, from the measurements of the NO level and air flow rate. This model provides an accurate description of the flow-dependent NO production on the basis of one inflammation parameter only, the maximum airway wall flux of NO, which means that a one-parameter analysis to the tidal breathing data becomes possible. The use of this model is particularly advantageous during the step of analyzing.

Preferably, in this embodiment, the parameter $D_{ax}$ is a constant value and $c_3$ and $c_4$ are set to respective constant values based on a population value or a previous personal value for the subject.

In certain embodiments, the step of analyzing comprises dividing each exhalation into a plurality of exhalation parts; for each exhalation part, determining values for a flow independent parameter using the measurements of NO levels and flow rate obtained during that exhalation part; for each exhalation part, calculating the spread of the determined values for the flow independent parameter; and performing a first discarding step in which any exhalation part where the calculated spread deviates from a predetermined value by more than a threshold value is discarded; wherein the step of determining a value for the at least one parameter relating to NO in the lower respiratory tract of the subject uses the measurements of NO levels and/or air flow rate for exhalation parts remaining after the first discarding step. This results in exhalation parts being discarded where the parameter value varies more than can be expected for an uncontaminated exhalation.

Preferably, the threshold value is determined based on the noise in the measurements of air flow rate and NO level.

In certain embodiments, the step of analyzing further comprises, for each remaining exhalation part, determining the average value of the determined values for the flow independent parameter; identifying the remaining exhalation part having the lowest average value for the flow independent parameter; and performing a second discarding step in which any exhalation part whose average value for the parameter value deviates from the average value for the parameter value for the identified exhalation part by more than a threshold value is discarded; wherein the step of determining a value for the parameter relating to NO in the lower respiratory tract of the subject uses the measurements of NO levels and/or air flow rate for the exhalation parts remaining after the second discarding step. As the exhalation part having the lowest average for the parameter value is likely to be from the exhalation that has the least (or no) NO contamination from other sources, it can be used as a basis for identifying and discarding exhalation parts where there is consistent NO contamination throughout the exhalation.

A further aspect of the invention provides a computer program product comprising computer readable code configured to cause a computer, processor or computer system to perform the method described above.

Yet another aspect of the invention provides an apparatus for determining a value for at least one parameter relating to nitric oxide, NO, production in the lower respiratory tract of a subject, the apparatus comprising an NO sensor for taking a plurality of measurements of the level of NO in air exhaled by the subject during multiple exhalations of a tidal breathing manoeuvre; a flow rate sensor for taking a plurality of measurements of the flow rate of air exhaled during the multiple exhalations of the tidal breathing manoeuvre; and a processor that is configured to receive the measurements of NO level and flow rate, analyze the measurements to identify exhalations where the NO produced in the lower respiratory tract dominates the NO contribution from other sources, and determine a value for the parameter relating to NO in the lower respiratory tract of the subject from the measurements of NO levels and/or air flow rate obtained during the identified exhalation parts.

In certain embodiments, the processor is configured to analyze the measurements by dividing each exhalation into a plurality of exhalation parts; for each exhalation part, determining values for a flow independent parameter using the measurements of NO levels and flow rate obtained during that exhalation part; for each exhalation part, calculating the spread of the determined values for the flow independent parameter; and performing a first discarding step in which any exhalation part where the calculated spread deviates from a predetermined value by more than a threshold value is discarded; wherein the step of determining a value for the parameter relating to NO in the lower respiratory tract of the subject uses the measurements of NO levels and/or air flow rate for the exhalation parts remaining after the first discarding step.

In certain embodiments, the processor is further configured to analyze the measurements by for each remaining exhalation part, determining the average value of the determined values for the flow independent parameter; identifying the remaining exhalation part having the lowest average value of the determined values for the flow independent parameter; and performing a second discarding step in which any exhalation part whose average value for the parameter value deviates from the average value for the parameter value for the identified exhalation part by more than a threshold value is discarded; wherein the step of determining a value for the parameter relating to NO in the lower respiratory tract of the subject uses the measurements of NO levels and/or air flow rate for the exhalation parts remaining after the second discarding step.

BRIEF DESCRIPTION OF THE DRAWINGS

Preferred embodiments of the invention will now be described, by way of example only, with reference to the following drawings, in which.

DETAILED DESCRIPTION OF THE PREFERRED EMBODIMENTS

Figure 2:
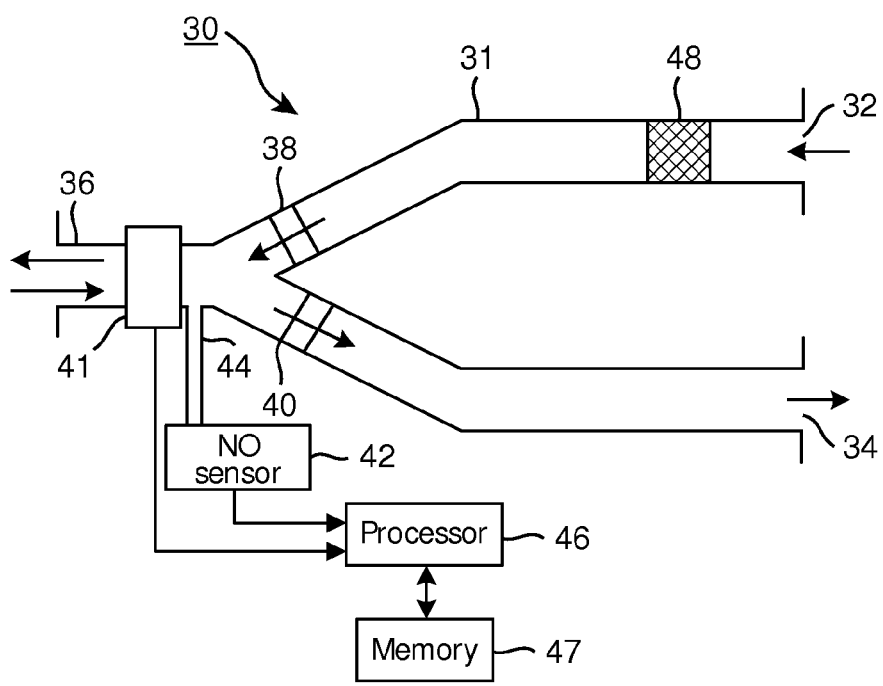
FIG. 2 is a block diagram of an apparatus according to the invention for measuring NO levels using a tidal breathing technique.

An apparatus in accordance with an embodiment of the invention for measuring NO levels in exhaled air during tidal breathing is shown in FIG. 2. The apparatus 30 comprises a tube 31 arranged in a generally 'Y' shape with the three ends forming an air inlet 32, an air outlet 34 and a mouthpiece 36 respectively. A first one-way valve 38 is provided in the tube 31 between the air inlet 32 and the mouthpiece 36 and a second one-way valve 40 is provided in the tube 31 between the mouthpiece 36 and the air outlet 34. The one-way valves 38, 40 are configured so that air is drawn through the tube 31 via the air inlet 32 and mouthpiece 36 when the subject inhales, and air is passed through the tube 31 via the mouthpiece 36 and air outlet 34 when the subject exhales.

A flow rate sensor 41, for instance a differential pressure sensor that measures a pressure drop over a minimal restriction in the exhalation path, is provided near to the mouthpiece 36 for measuring the flow rate of the exhaled air (the flow rate sensor 41 could alternatively be located in the tube 31 between the mouthpiece and air outlet 34). Instead of measuring a pressure difference, the flow rate sensor 41 can be based on an ultrasonic sensor, in which case no restriction is required in the flow path. A NO sensor 42 for measuring levels of NO in the exhaled air is connected to a side stream 44 with a connection to the main exhalation stream preferably close to the mouth piece. The NO sensor 42 should be capable of measuring low concentrations of NO at a sufficiently high time resolution in order to capture the variation in NO levels during the tidal breathing pattern accurately. In a preferred embodiment, the NO sensor 42 is a chemiluminescent analyzer. Alternatively, the NO levels can be measured using a photo-acoustic $NO_2$ sensor in combination with a $NO$-to-$NO_2$ converter.

It should be noted that the different path lengths to the NO sensor 42 and the flow rate sensor 41 as well as delays in the NO detection may result in a relative delay in the operation of these sensors, so there may be a need to apply a correction to the timings of the relative measurements to ensure that the measurements correspond to one another.

A processor 46 is connected to the flow rate sensor 41 and NO sensor 42 so that it receives a time series of measurements of the flow rate of the exhaled air and the NO levels in the exhaled air. The processor 46 processes these measurements to determine a value for one or more flow independent parameters related to NO production in the lower respiratory tract of the subject, as described further below.

When the apparatus 30 is in use, the subject breathes normally and NO levels and corresponding flow rates are recorded for a plurality of exhalations. Preferably measurements are acquired during a measurement period of about 30 seconds to one minute to enable enough NO and flow measurement data for the analysis.

The processor may be coupled to a memory 47 for storing data. If the subject under test has previously been tested the memory 47 may store some personal information about that subject and may store values for various model parameters which are appropriate for that subject. The memory 47 may also store general or specific population averaged values for various model parameters. The memory 47 may be integrated with the processor 46 or may be a removable memory apparatus.

A NO filter 48 can be provided in the tube 31 between the air inlet 32 and the first one-way valve 38 that removes NO from the air drawn into the apparatus 30 from the surrounding environment when the subject inhales.

Figure 1:
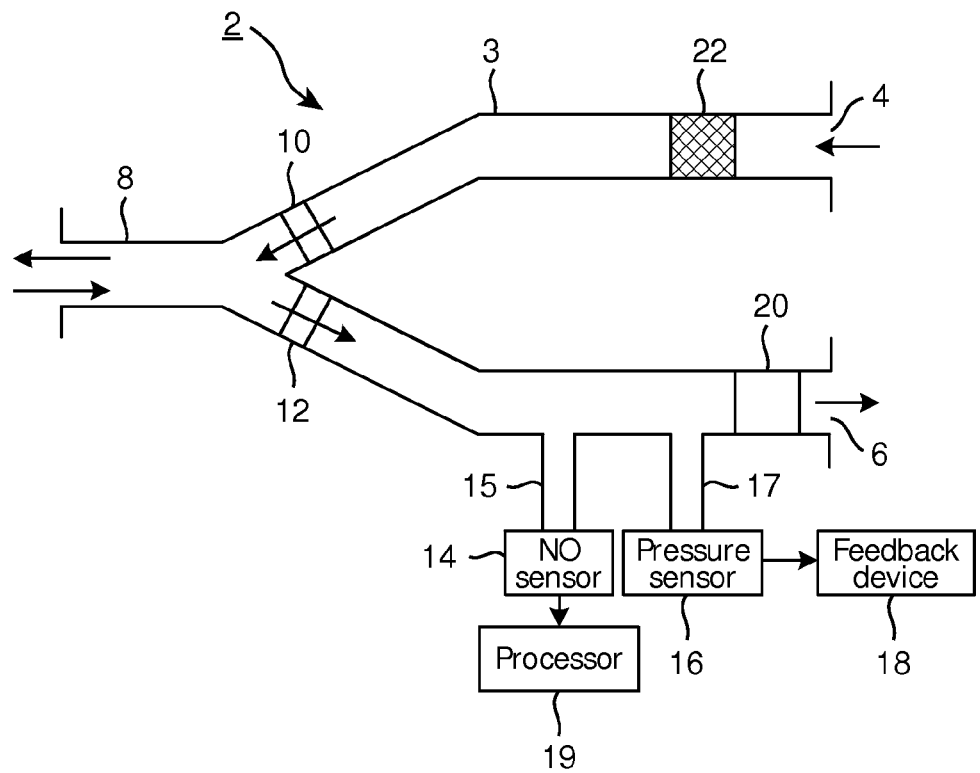
FIG. 1 is a block diagram of a conventional apparatus for measuring NO levels using a fixed flow rate technique.

Unlike with the fixed flow rate apparatus 2 shown in FIG. 1, it is not essential to provide a flow restrictor in the tube 31 between the second one-way valve 40 and the air outlet 34 as in the fixed flow rate apparatus 2. However, a small restriction can be included to increase the pressure and thus the concentration of NO in the air sampled by the NO sensor 42, thereby increasing the accuracy of the processor output.

Although not shown in FIG. 2, where the apparatus 2 provides measurements of NO levels in real-time or near real-time, the apparatus 2 could be provided with a feedback unit for providing audio and/or visual feedback to the subject once a sufficient number of breaths or an acceptable number of data points have been collected.

The operation of the processor 46 according to the invention will now be described in more detail with reference to the flow charts shown in FIGS. 3 and 4. Firstly, in step 101 of FIG. 3, the processor 46 obtains a plurality of measurements of NO levels and the corresponding air flow rates covering a number of exhalations by a subject performing a tidal breathing manoeuvre.

As described above, it has been found that some exhalations during tidal breathing provide an accurate representation of the NO produced in the lower respiratory tract, while other exhalations during tidal breathing are contaminated with NO from other sources and provide an inaccurate value. So, in accordance with the invention, the processor 46 analyses the measurements to identify those exhalations or parts of the exhalations where the NO produced in the lower respiratory tract dominates the NO measurement contribution from other sources, such as the environment or nasal cavity of the subject (step 103).

The processor 46 then uses the measurements for part or all of the identified exhalations (i.e. those exhalations where the NO produced in the lower respiratory tract dominates the NO measurement contribution from other sources) to determine values for one or more flow independent parameters related to NO production in the lower respiratory tract of the subject (step 105).

In preferred embodiments of the invention, the identification in step 103 and subsequent determining in step 105 can make use of a model or a combination of models that describe the production, diffusion and/or removal of NO in the lower respiratory tract of the subject. In the identification step, use can be made of the fact that the NO produced in the lower respiratory tract has a specific flow dependence which is disrupted when NO from other sources is present. Preferably a model with a single free parameter is used in the identification step and statistical measures are applied to identify those parts of the exhalation where the NO from the lower respiratory tract dominates. During the determining step all identified parts of the exhalations are used in an analysis with either the same single parameter model or a model with more free parameters.

Various different models of NO production and diffusion in the lungs are known and can be used as the model describing flow dependence of exhaled NO. Key elements in these models are: i) a description of the geometry of the lung system, often in simplified compartment form, ii) NO generation, and iii) NO diffusion. For instance a two-compartment model of NO exchange dynamics represents the lungs by a rigid airway compartment and a flexible alveolar compartment—see for example Tsoukias et al. "A two-compartment model of pulmonary nitric oxide exchange dynamics" J. Appl. Physiol, Vol. 85, pp 653-999, 1998. A three compartment model is described in "Characterizing airway and alveolar nitric oxide exchange during tidal breathing using a three-compartment model", P. Condorelli et al., J. Appl. Physiol. Vol 96, pp 1832-1842, 2004. Another model is a trumpet model with axial diffusion which takes account of the trumpet shape of the airways and assumes that axial diffusion is the dominating NO diffusion mechanism—see US2007/0282214 or P. Condorelli et al., J. Appl. Physiol. Vol 102, pp 417-425, 2007 for example. The trumpet model with axial diffusion can provide a good description of the flow dependent NO production in the lungs but is mathematically more complex than the two and three compartment models and requires use of approximate analytical solutions or numerical solutions. All the aforementioned models form approximations to a more general model describing the generation and transport of various gasses in the airway system by a partial differential convective diffusion equation where the 3-dimensional asymmetric airway structure is mapped into the flow through an axially symmetric tube with a varying diameter.

The models describing the flow dependence of exhaled NO generally are based on various flow independent parameters. The two compartment model for example has three flow independent parameters, the steady state alveolar concentration, the airway wall diffusing capacity and the airway wall concentration (alternatively, instead of the airway wall concentration parameter, the maximum airway wall flux of NO can also be used). The steady state alveolar concentration and airway wall concentration will vary with the severity of any airway inflammation whereas the airway wall diffusing capacity is a gas diffusion parameter related to the transfer of NO between airway wall and gas stream and differs only slightly for healthy and asthmatic people. The Condorelli approximation to the trumpet model with axial diffusion has three flow independent parameters, two of which vary with the severity of inflammation of the lungs, i.e. the steady state alveolar concentration and maximum airway wall flux of NO and one describing the axial gas diffusion. Although the flow-independent parameters linked to the severity of inflammation from the two-compartment model and axial diffusion dominated trumpet model have similar names their actual values are model dependent and values can only be converted in a simple way within a certain flow range.

In general, values for the various parameters in the model describing the NO production in the lower respiratory tract are not known in advance for a specific subject. Therefore, in embodiments of the invention, the model used by the processor 46 can be set-up in a way such that flow dependent NO production is described to a reasonable accuracy by a single unknown parameter.

This can be achieved by setting parameters with small variability to average values leaving a single inflammation related parameter as the remaining unknown parameter. For example, at least one of the parameters of the model relating to gas diffusion and/or at least one other parameter related to inflammation can be set to a constant value. At least one of the parameters may be set to population average values, i.e. an average value that has previously been determined for the population. For some parameters, different population average values may exist based on gender, age, etc. and the appropriate value for the subject can be chosen. Setting these parameters to population averages obviously results in some inaccuracy but it has been found that sufficiently accurate values for the flow independent parameters may still be obtained. Additionally or alternatively at least one of the flow-independent parameters may be set to a personal value previously obtained or estimated for the particular test subject. A value for one or more flow independent parameters could be determined for the subject and used in all successive measurements.

The model therefore incorporates one or more flow independent parameters which vary with inflammation that are determined from the measurements of the level of exhaled NO and the corresponding flow rate. The remaining parameters are either set as constants, a population average relevant for the subject or a previously estimated or determined value for the subject.

The two compartment model mentioned above describes the lungs as a cylindrical rigid airway compartment with a volume of around 150 ml and a flexible alveolar compartment. The airway compartment is described by two parameters, the airway diffusing capacity and either the airway wall concentration of NO or maximum airway wall flux of NO. The alveolar compartment is described by a single parameter, the steady state alveolar concentration of NO. The exhaled NO concentration $C_E$ as a function of the flow $\dot{V}$ according to the two compartment model is given by:

$$C_E = C_w \cdot (1 - e^{-D_{aw}/\dot{V}}) + C_{alv} \cdot e^{-D_{aw}/\dot{V}} \quad (1)$$

Thus, the exhaled NO concentration depends on the wall concentration $C_w$ and alveolar concentration $C_{alv}$ weighted by terms that depend on the airway diffusion coefficient $D_{aw}$ and the flow. The analytical expression is valid for all relevant flows i.e. from above the tidal breathing regime to below 50 ml/s.

In clinical studies it has been observed that the airway diffusing capacity is not directly related to inflammation severity. Therefore the airway diffusing capacity can be estimated based on population averages. In case the tidal breathing NO measurement device is used for repeated measurements of an already diagnosed asthmatic individual, a population average value for asthmatic persons of $D_{aw}$ can be used. Alternatively the airway diffusing capacity for a particular subject may have been derived previously, for instance from different measurements, and may be entered into the processor 46 or obtained from memory 47.

In one embodiment, the steady-state NO concentration in the alveolar compartment, $C_{alv}$, can also be set to a separately determined individual value, which means that the processor 46 can determine values for the remaining flow independent inflammation related parameter (wall concentration $C_w$) using the measurements of the NO levels ($C_E$) and air flow rate ($\dot{V}$).

However, whilst the two compartment model can give satisfactory results with prior knowledge of the alveolar concentration, a model including axial diffusion is currently preferred as it can provide a sufficiently accurate description of the flow-dependent NO production on the basis of one inflammation parameter only, which is the maximum airway wall flux of NO. The axial gas diffusion constant is to a large extent a general gas diffusion constant. Application of a model where the inflammation is described by one dominating parameter has the main advantage that a one-parameter analysis to the tidal breathing data becomes possible. The latter is an advantageous feature during the final analysis of the data within the selected exhalations or exhalation parts, but it forms a highly preferred analysis approach for the first stage of selection of contaminated and non-contaminated parts.

The trumpet model as, for instance, described in US2007/0282214 is an example of a model including axial diffusion, maximum airway wall flux of NO and a steady state alveolar concentration. This model can be further extended to include the airway diffusing capacity and for instance a maximum airway wall flux of NO that depends on the axial position in the airway tree. It should be noted that the values of the maximum airway wall flux of NO, steady state alveolar NO concentration and NO diffusing capacity for a model including axial diffusion cannot be directly compared to their value in for instance a two-compartment model without axial diffusion.

Trumpet models including axial diffusion are defined by a differential equation, a source term describing the NO production, boundary conditions to the alveolar and mouth region and a description of the trumpet shape. A general solution is not known but a numerical solution can be obtained when all the parameter values are known. A determination of one or more parameter values from experimental data becomes only possible on basis of an approximate analytical solution or a time-consuming and complex iterative numerical procedure.

US2007/0282214 discloses a linear approximation of the flow-dependent NO production for a trumpet model including a maximum airway wall flux of NO, steady state alveolar value and axial diffusion. The linear approximation is valid in the flow-range of 100-250 ml/s. Most tidal breathing manoeuvres are within this flow range but for some subjects, tidal breathing involves higher flows.

Comparing numerical solutions and analytical approximations for typical values for the trumpet model parameters, the present inventors have found that the following analytical expression describes the NO production $C_E$ as a function of flow $\dot{V}$ for flows of 25 ml/s and above quite accurately:

$$C_E = C_{alv} + \frac{J_{aw}}{\dot{V}} \left(1 + \frac{c_1 \cdot D_{aw}}{\dot{V}}\right)^{-c_2} \left(1 + \frac{c_3 \cdot D_{ax}}{\dot{V}}\right)^{-c_4} \quad (2)$$

where $\dot{V}$ denotes the flow rate of exhaled air, $D_{aw}$ the airway wall diffusion coefficient and $D_{ax}$ the axial diffusion constant for Nitric Oxide. $C_{alv}$ is a flow independent contribution relating the steady state alveolar NO concentration. $c_1$, $c_2$, $c_3$ and $c_4$ are positive constants which are derived from fits to numerical solutions of a differential equation describing nitric oxide production, convection and diffusion in the airway tree. In one model, $c_1$ may have a value of around 1, $c_2$ may have a value of 0.4, $c_3$ may have a value around 2200 ml/cm$^2$ and $c_4$ may have a value of around 0.25.

For flows around 50 ml/s and above, and the time scale involved in tidal breathing, $D_{aw}$ and the steady state alveolar value $C_{alv}$ can be set to zero. 0.23 cm$^2$/s can be used as a typical value for $D_{ax}$ (The Properties of Gases and Liquids, RC Reid et al., New York: McGraw-Hill, 1988).

$J_{aw}$ is the maximum airway wall NO flux, a flow independent parameter which is particular to the subject and which the processor 46 determines from the measurements of exhaled NO level and flow rate.

The approximated analytical solution given above is based on the finding that (a product) of diffusion terms of the form:

$$\left(1 + \frac{k_1 D_i}{\dot{V}}\right)^{-k_2} \quad (3)$$

with $k_1$ and $k_2$ constant, provides a good description of the flow dependent NO production in the trumpet shaped airway. An analytical approximation is very powerful in the analysis of the measurement data because it enables a simple and fast determination of one or more flow-independent parameter(s) from experimental data.

In one embodiment, where the apparatus 30 according to the invention is to be used in a professional care setting for evaluating the lung inflammation of various subjects, the flow-independent parameters $D_{aw}$ and $C_{alv}$ can be set to population averaged values leaving $J_{aw}$ as the single unknown inflammation related parameter. Alternatively, where the apparatus 30 is to be used by an individual subject (i.e. by a subject monitoring their asthma in a home setting, say), the values of $D_{ax}$, $D_{aw}$ and $C_{alv}$ for the subject can be derived following analysis of the subject by a pulmonologist (perhaps by using the conventional fixed-flow exhalation measurement technique). As a further alternative, following diagnosis of asthma, the parameters $D_{ax}$ and $D_{aw}$ can be set to population averaged values for people with asthma.

For the two compartment model, an analysis with a single inflammation related parameter becomes possible by using a fixed ratio of the alveolar concentration and the wall concentration $C_{alv}/C_w$ (or $C_{alv}/J_{aw}$). This ratio can either be based on a population average or derived from axial diffusion i.e. a by linking the two-compartment model parameters to the trumpet model parameters in the tidal breathing flow range.

Step 103 of FIG. 3 will now be described in more detail with reference to the graphs in FIG. 4 and the flow chart in FIG. 5.

For the analysis and determining steps, each exhalation is split into parts (for example initial, intermediate and final parts) in a predefined way. A preferred embodiment is shown in FIG. 4. The measured eNO and flow profiles for exhalation i are shown in FIGS. 4(a) and 4(b) as a function of time. Any time delay between the eNO and flow measurements resulting from gas transport, dead volumes and NO sensor delay should be taken into account. The exhalation volume versus time as shown in FIG. 4(c) is obtained by integration of the flow profile from the beginning at $t^i_b$ to the end $t^i_e$. The maximum exhaled volume $V^i_{max}$ for exhalation i is reached at $t^i_e$. Subsequently, to split the profile for an exhalation into three parts, time $t^i_1$ indicating the end of an initial part of the exhalation and time $t^i_2$ indicating the start of a final part of the exhalation can be determined corresponding to for instance 30% and 80% of the maximum exhaled volume respectively. The first part of the eNO and flow profile now corresponds to time frame $t^i_b$-$t^i_1$, the second part to $t^i_1$-$t^i_2$ and the third part to $t^i_2$-$t^i_e$. If advantageous, the fractions of the maximum volume or the number of parts can be chosen differently.

Figure 4:
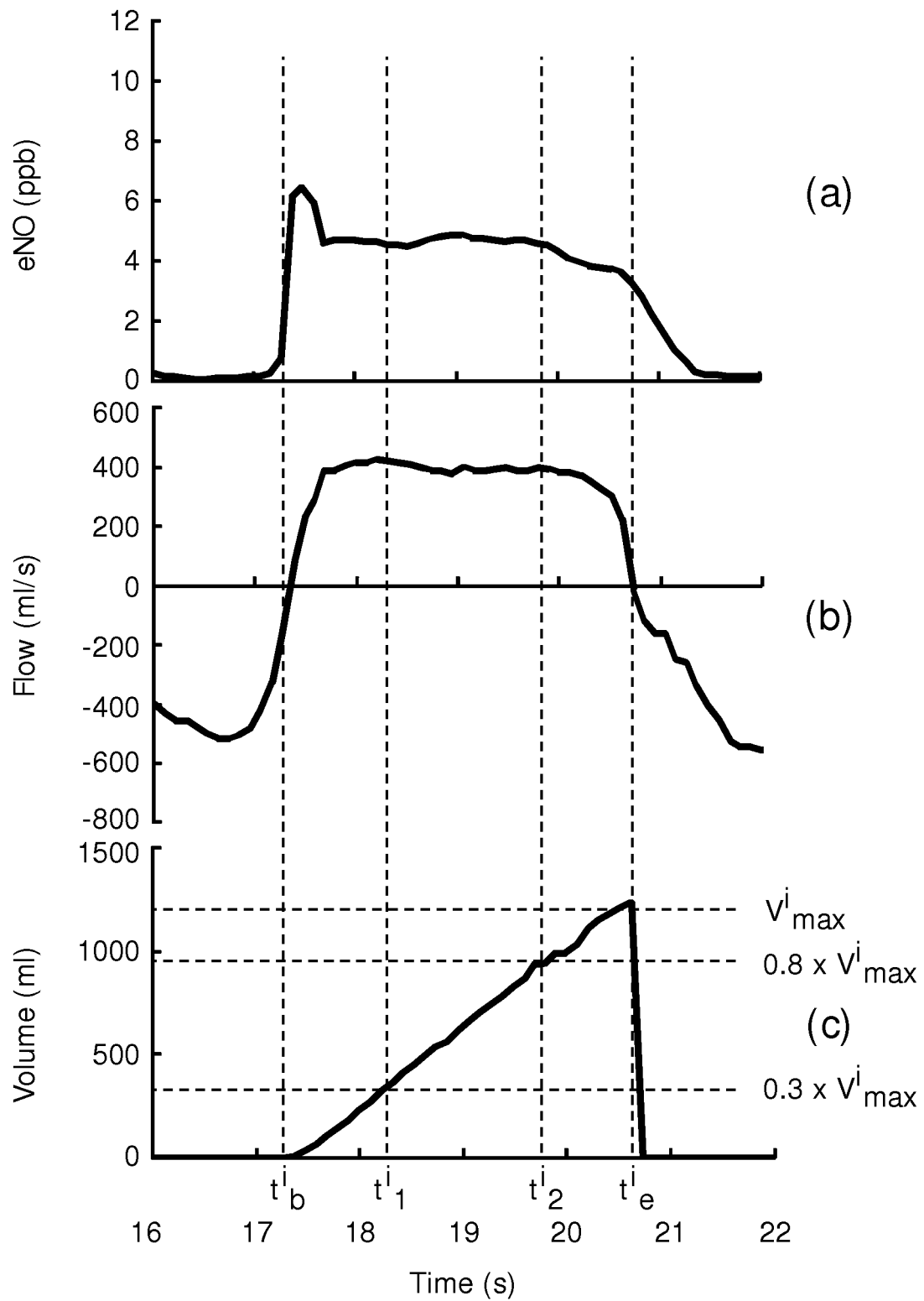
FIG. 4(a-c) are graphs illustrating how an exhalation can be divided into parts.
Figure 5:
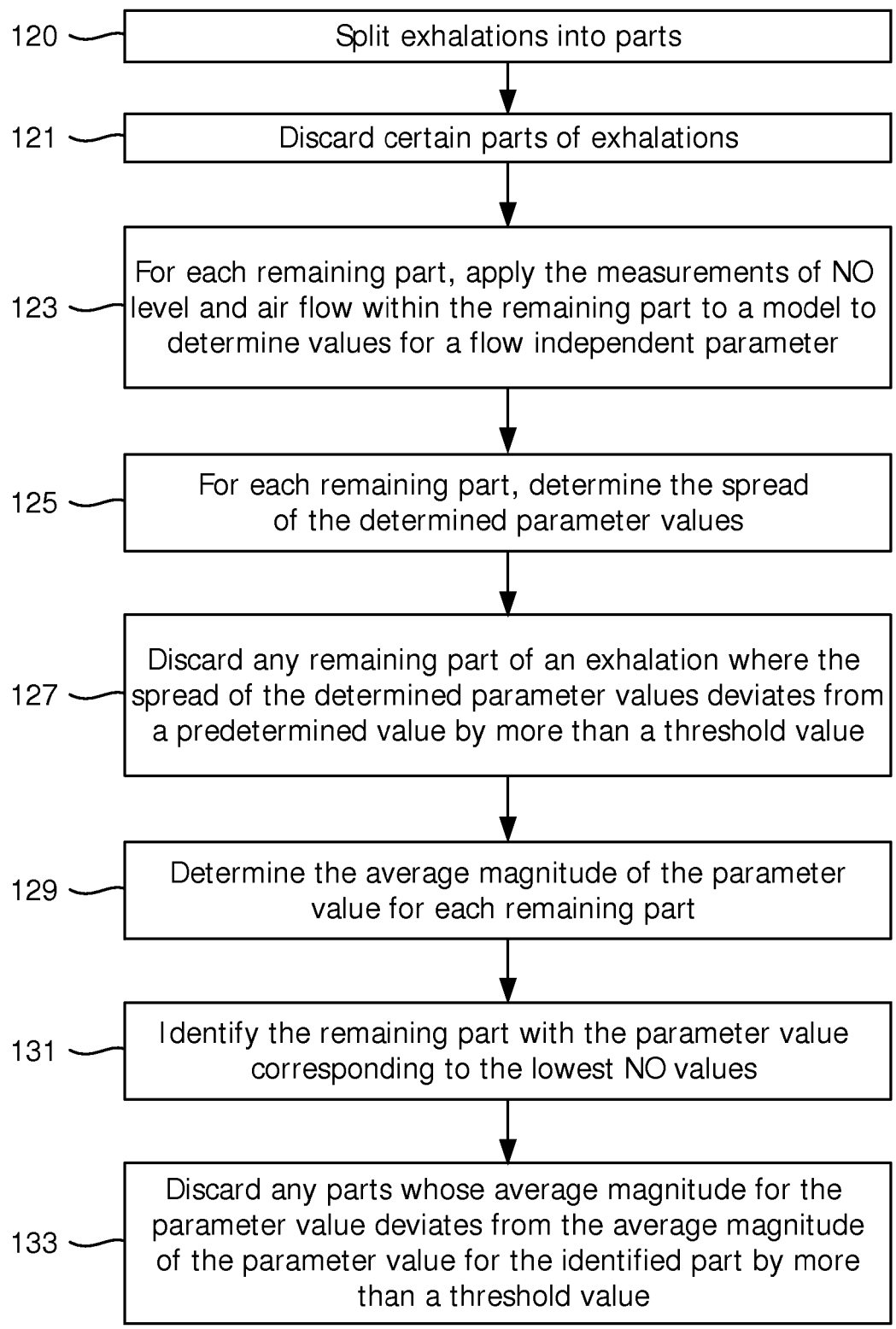
FIG. 5 is a flow chart illustrating the step of analyzing in FIG. 3 in more detail.

FIG. 5 shows the analysis steps in more detail. Firstly, in step 120 all the exhalations are divided into the predefined parts as shown in FIG. 4. In step 121 of FIG. 5, the processor 46 discards all parts of the first exhalation in the tidal breathing manoeuvre, and some parts of each subsequent exhalation, for instance the initial and final parts. It can be seen in the graphs of FIGS. 6(a) and (b) in which the exhaled NO levels are plotted against time that the measured NO levels (represented by the dashed line) are often higher at the start of an exhalation. A small increase in agreement with the models, is expected due to the increased residence time in the airways around the transition from inhalation to exhalation. However, larger peaks are often observed at the beginning and end of the exhalation and are due to nasal NO contamination during the low exhalation flows around the transition from inhalation to exhalation and exhalation to inhalation. Therefore it is useful to discard the measurements at the beginning and end of each exhalation from subsequent analysis. "Discarding" measurements or parts can comprise deleting the measurements for that part from the memory 47 or labeling the measurements for that part in the memory 47 appropriately so that they are not used during later processing steps. Each exhalation part that is not discarded in step 121 is referred to as a remaining part in the following explanation of FIG. 5.

Then, in step 123, the processor 46 applies the measurements of the exhaled NO level and flow rate for the remaining (i.e. non-discarded) part or parts of each exhalation to the selected model to determine values for the flow-independent parameter. For example, if the trumpet model described above is used, the processor 46 will determine values for the maximum airway wall NO flux, $J_{aw}$ in this step.

Next, for each exhalation part, the processor 46 determines the variation or spread in the parameter value across the exhalation part (step 125). Techniques for determining the variation or spread of a set of data values are well known in mathematics and will not be described in any further detail herein.

It is expected that there will be a relatively small spread in the parameter value across the exhalation part when the measurement of the exhaled NO is dominated by NO generated in the lower respiratory tract. In particular, for an uncontaminated exhalation, the spread in the parameter value should roughly correspond to the noise in the flow rate and NO measurements and the inaccuracy that arises from approximating values for the other parameters in the model. Therefore, where the spread in the parameter value for an exhalation part exceeds a predetermined value, the processor 46 discards that exhalation part from further analysis (step 127). For instance, the exhalation part can be discarded when the standard deviation is larger than 2 times the standard deviation based on the noise level in the NO and flow measurement.

Figure 3:
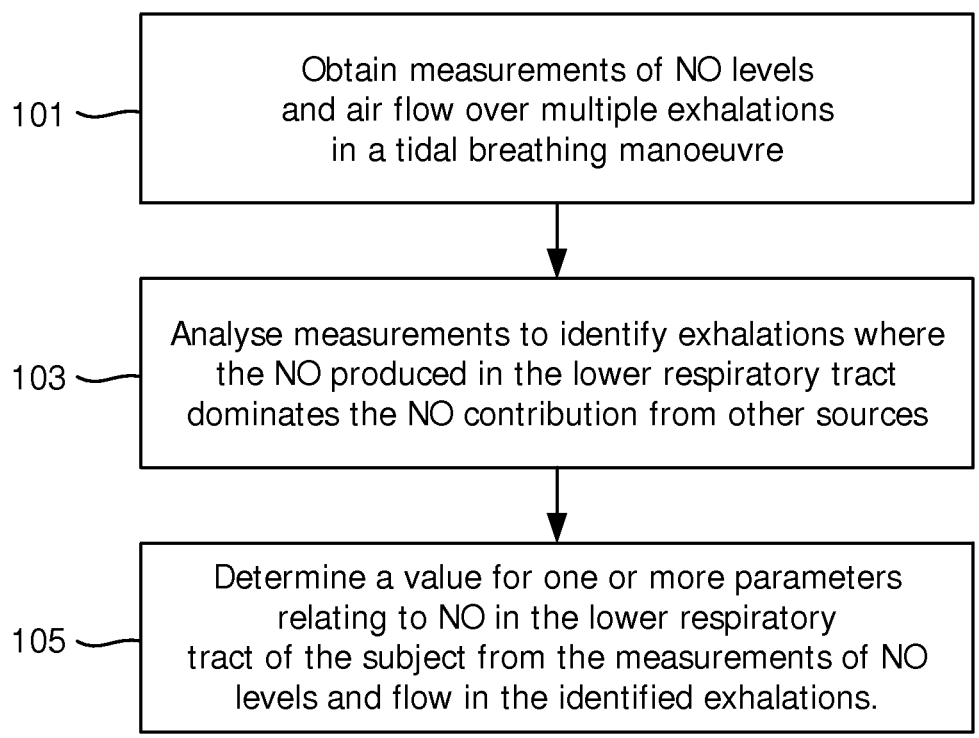
FIG. 3 is a flow chart of an exemplary method according to the invention.

In some embodiments of the invention, step 127 can conclude the analysis step (step 103 of FIG. 3) and the processor 46 can use the measurements for exhalations having remaining parts to determine the required parameter values in step 105 of FIG. 3.

However, in other embodiments of the invention, the processor 46 can carry out additional analysis to determine whether any further (parts of the) exhalations need to be excluded. In particular, in step 129, the processor 46 determines the average magnitude of the parameter value for each exhalation part remaining in the analysis.

It is understood that the exhalation(s) having the parameter values corresponding to the lowest NO values are, most likely, not contaminated. Therefore, the average magnitude of the parameter value for a specific remaining exhalation part is compared to the average magnitude of the parameter value for other remaining (non-discarded) parts, and where the average parameter value deviates significantly from this value that exhalation part is discarded from further analysis.

In particular, in step 131, the processor 46 identifies the remaining part with the parameter value corresponding to the lowest exhaled NO measurements, and, in step 133, discards any other remaining parts whose average magnitude for the parameter value deviates from the average magnitude of the parameter value for the identified part by more than a threshold value. For instance, an exhalation part can be discarded when the average parameter value for that part differs from the average parameter value for the identified exhalation part by more than 0.3 times the average parameter value for the identified exhalation part.

The processor 46 can then use the measurements for the remaining parts of the exhalations to determine the required parameter values in step 105 of FIG. 3.

In further embodiments of the invention, as it is possible for the removal of environmental and nasal NO in the respiratory tract during inhalation to be described by a model representing the mixing and diffusion process in the alveolar part, it is possible for the processor 46 to take the inhalation into account in order to determine whether an exhalation or an extended initial part of an exhalation has to be discarded from further analysis.

The operation of the processing method described above can be seen in FIGS. 6(*a*) and (*b*). These graphs show the exhaled NO measurement data for two separate tidal breathing manoeuvres comprising five exhalations. The measurements of the exhaled eNO are represented by the dashed lines.

In this illustrated embodiment, the processor 46 is using the trumpet model and values for all of the flow independent parameters have been separately determined and the measurements of flow rate are used as the input to the model in order to calculate expected values for the exhaled NO measurements.

Figure 6:
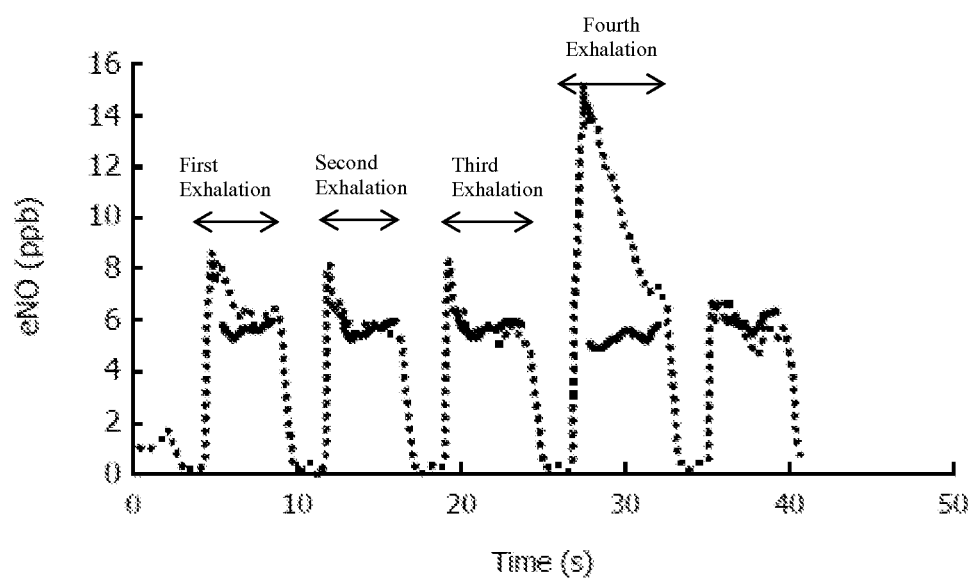
FIGS. 6(a) and 6(b) are graphs illustrating measured nitric oxide levels and calculated nitric oxide levels for a number of exhalations.
Figure 6:
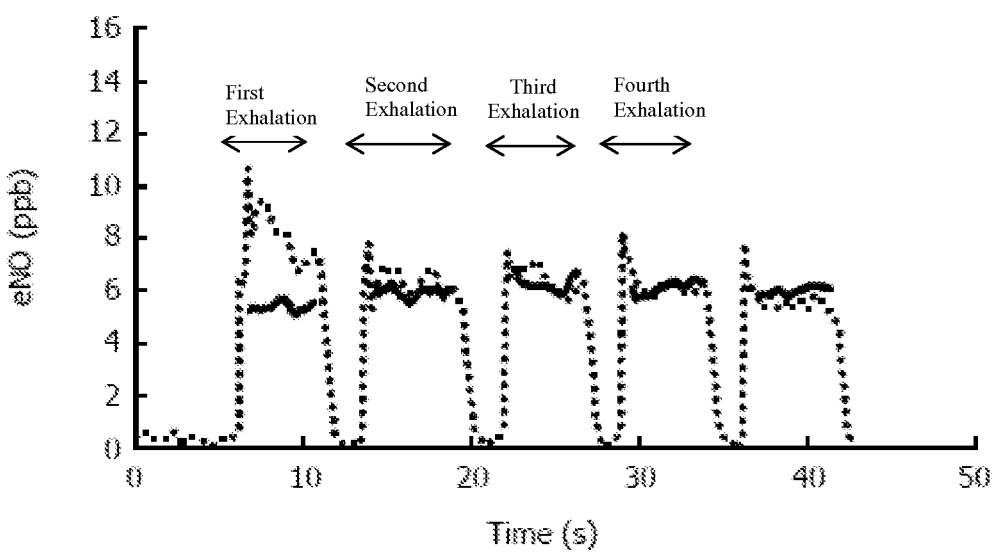

Therefore, following the method in FIG. 5 above, the processor 46 determines values for the exhaled NO using the flow rate measurements in the remaining parts and the model (the determined values are shown in FIGS. 6(*a*) and (*b*) by the solid lines).

It is clear from FIG. 6 that significant deviations occur between the measured NO levels and the expected NO levels for the fourth exhalation in FIG. 6(*a*) and the first exhalation in FIG. 6(*b*). By following the steps in FIG. 5, the processor 46 will discard the measurements for these exhalations from subsequent analysis.

In the fourth exhalation of FIG. 6(*a*), a deviation from the determined NO value is seen which is large in the beginning of the exhalation, and becoming smaller towards the end of the exhalation. In this case, a small percentage of the air has probably been inhaled through the nose and has not reached the lower parts of the lung that are effective in NO removal.

The offset in the first exhalation in FIG. 6(*b*) is understood as being due to the shallow inhalation and incomplete removal of NO in the alveolar part of the lung of environmental or nasal NO inhaled from a previous breath cycle.

Figure 7:
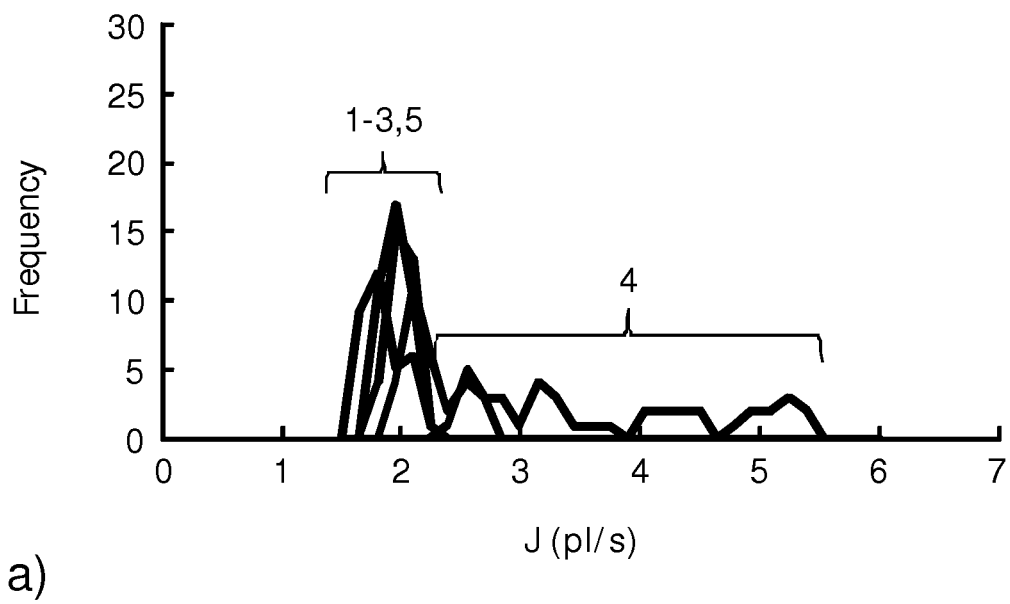
FIGS. 7(a) and 7(b) show histograms for the exhalations in FIGS. 6(a) and 6(b) respectively.
Figure 7:
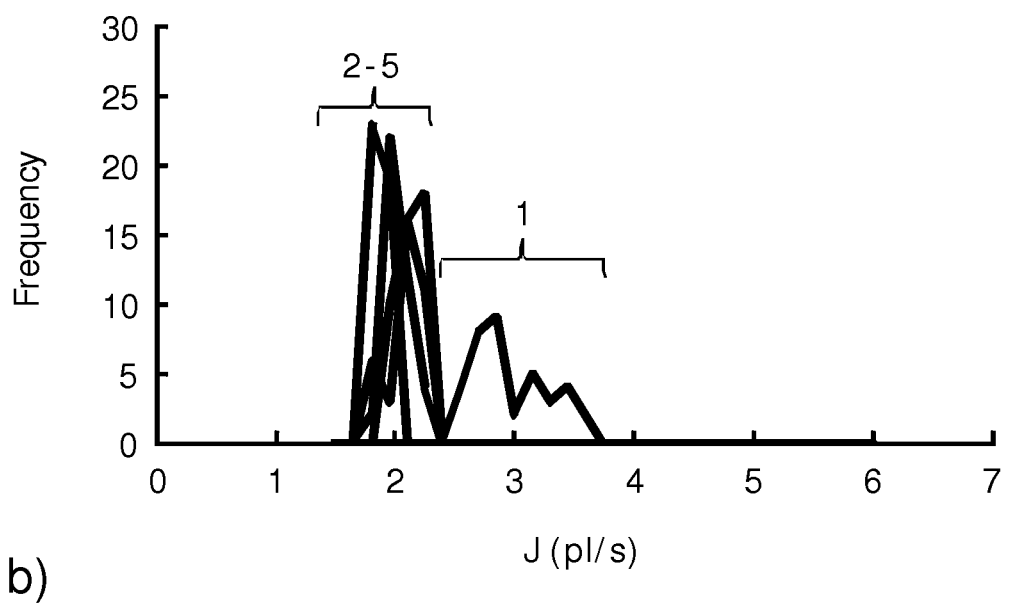

FIG. 7 illustrates the method by means of histograms. By using the two-compartment model or trumpet model with $J_{aw}$ as the single unknown parameter (where $J_{aw}$ is given by $D_{aw}C_w$ in equation (1)), the value of $J_{aw}$ can be determined using the exhaled NO and flow rate measurements within a certain range of exhaled volumes (for instance 30-80% of the maximum exhaled volume for each exhalation) and a histogram can be compiled from the $J_{aw}$ values for every exhalation (or exhalation part). FIGS. 7(*a*) and (*b*) show the histograms for the measurement data shown in FIGS. 6(*a*) and (*b*) respectively.

In the histograms shown, bins of 0.15 pico-liters/second (pl/s) are used. The values of $J_{aw}$ for each exhalation part are put into the relevant bins, and the lines in the graphs represent individual exhalation parts shown in FIG. 6.

Exhalation parts can be accepted as non-contaminated based on the width of the histogram for that exhalation part being within a certain value and/or the average value for $J_{aw}$ in that exhalation part being within a certain range of the overall average $J_{aw}$ (or minimum average $J_{aw}$) of all the remaining exhalation parts. For example, it can be seen in FIG. 7(*a*) that the spread in $J_{aw}$ values for the remaining part of the fourth exhalation is large, so without knowledge of the subject's $J_{aw}$ parameter, this exhalation can be discarded from further analysis.

Although the spread in $J_{aw}$ values for the remaining part of the first exhalation in FIG. 7(*b*) is slightly higher than the spread for the remaining parts of the other exhalations, this might not be sufficient to take a decision to discard this exhalation. In this case, it might be necessary to perform a comparison with the average values for the other exhalation parts in order to determine whether this exhalation should be discarded.

It will be appreciated that the invention described above can be used with currently available eNO measurement systems, provided that the sensors in these systems have a sufficient time resolution (i.e. a short enough response time) to measure the NO patterns during tidal breathing. As indicated above, such sensors include chemiluminescent analyzers.

Although the invention has been described in terms of a method performed by a processor in a measurement apparatus, it will be appreciated that the invention can be performed by a suitably programmed computer and therefore the invention can also comprise a computer program which, when run on a suitable computer or computer system and given the plurality of measurements as a data input, performs the method described above. The computer program may be stored on a computer readable storage medium, for example a hard disk, an optical disk or a memory card.

Thus, there is provided a method and apparatus that can measure NO in exhaled air during a tidal breathing manoeuvre and that mitigates the problems with contamination of the exhaled air with inhaled NO from the nasal cavity.

While the invention has been illustrated and described in detail in the drawings and foregoing description, such illustration and description are to be considered illustrative or exemplary and not restrictive; the invention is not limited to the disclosed embodiments.

Variations to the disclosed embodiments can be understood and effected by those skilled in the art in practicing the claimed invention, from a study of the drawings, the disclosure, and the appended claims. In the claims, the word "comprising" does not exclude other elements or steps, and the indefinite article "a" or "an" does not exclude a plurality. A single processor or other unit may fulfill the functions of several items recited in the claims. The mere fact that certain measures are recited in mutually different dependent claims does not indicate that a combination of these measures cannot be used to advantage. A computer program may be stored/distributed on a suitable medium, such as an optical storage medium or a solid-state medium supplied together with or as part of other hardware, but may also be distributed in other forms, such as via the Internet or other wired or wireless telecommunication systems. Any reference signs in the claims should not be construed as limiting the scope.

The invention claimed is:

1. A method of determining at least one parameter value relating to nitric oxide, NO, production in the lower respiratory tract of a subject, using an apparatus including a NO sensor, a flow rate sensor and a processor, the method comprising:

obtaining, with the NO sensor and the flow rate sensor, a plurality of measurements of NO levels in exhaled air and air flow rate during multiple exhalations of a subject performing tidal breathing;

analyzing, with the processor, the plurality of measurements to identify exhalations where the NO produced in the lower respiratory tract dominates the NO contribution from other sources; wherein analyzing comprises:

separating individual exhalations into a plurality of exhalation parts;

for each individual exhalation part, determining values for a flow independent parameter, wherein the flow independent parameter is an airway wall concentration of NO or a maximum airway wall flux of NO, using the measurements of NO levels and flow rate obtained during that exhalation part;

for the individual exhalation parts, determining the average value of the determined values for the flow independent parameter;

identifying an exhalation part having the lowest average value;

discarding any exhalation part whose average value for the flow independent parameter deviates from the lowest average value by more than a threshold value; and identifying the exhalation parts remaining as exhalations where the NO produced in the lower respiratory tract dominates the NO contribution from other sources;

determining, with the processor, the flow independent parameter from the measurements of NO levels and/or air flow rate of each of the exhalation parts remaining; and outputting, with the processor, the determined values of the flow independent parameter of the exhalation parts remaining.

2. A method as claimed in claim 1, wherein determining values for the flow independent parameter for each individual exhalation part comprises using a model describing the flow dependence of NO levels in exhaled air.

3. A method as claimed in claim 2, wherein the model comprises one of a two-compartment model, three-compartment model, or a trumpet model.

4. A method as claimed in claim 2, wherein the model is a two-compartment model in which the exhaled NO concentration, CE, is given by $$C_E = C_w \cdot \left(1 - e^{-D_{aw}/\dot{V}}\right) + C_{alv} \cdot e^{-D_{aw}/\dot{V}}$$

where $C_{alv}$ is the alveolar concentration of NO, $D_{aw}$ is the airway diffusion coefficient, $\dot{V}$ is the air flow rate, the ratio of $C_{alv}/C_w$ and the value of $D_{aw}$ are set to constant values and wherein the step of analyzing comprises determining values for the wall concentration, $C_w$, from the measurements of the NO level and air flow rate.

5. A method as claimed in claim 4, wherein the ratio of $C_{alv}/C_w$ and $D_{aw}$ in the model are set to respective constant values based on a population value or a previous personal value for the subject.

6. A method as claimed in claim 2, wherein the model is a trumpet model in which the exhaled NO concentration, $C_E$, is given by $$C_E = \frac{J_{aw}}{\dot{V}}\left(1 + \frac{c_3 \cdot D_{ax}}{\dot{V}}\right)^{-c_4}$$

where $\dot{V}$ denotes the air flow rate, $D_{ax}$ the axial diffusion constant for Nitric Oxide, and $c_3$ and $c_4$ are positive constants and wherein the step of analyzing comprises determining values for the maximum airway wall NO flux, $J_{aw}$, from the measurements of the NO level and air flow rate.

7. A method as claimed in claim 6, wherein the parameter $D_{ax}$ is a constant value and $c_3$ and $c_4$ are set to respective constant values based on a population value or a previous personal value for the subject.

8. A method as claimed in claim 1, wherein the step of analyzing comprises:

for the individual exhalation parts, calculating the spread of the determined values for the flow independent parameter; and discarding any exhalation part where the calculated spread deviates from a predetermined value by more than a threshold value is discarded;

wherein the step of determining the average value of the determined values for the flow independent parameter uses the exhalation parts remaining after discarding the exhalation parts whose spread deviates.

9. A method as claimed in claim 8, wherein the threshold value is determined based on the noise in the measurements of air flow rate and NO level.

10. A tangible non-transitory computer program product comprising computer readable code configured to cause a computer, processor or computer system to perform the method claimed in claim 1.

11. An apparatus for determining a value for at least one parameter relating to nitric oxide, NO, production in the lower respiratory tract of a subject, the apparatus comprising:

an NO sensor for taking a plurality of measurements of the level of NO in air exhaled by the subject during multiple exhalations of a tidal breathing manoeuvre;

a flow rate sensor for taking a plurality of measurements of the flow rate of air exhaled during the multiple exhalations of the tidal breathing manoeuvre; and a processor that is configured to receive the measurements of NO level and flow rate, analyze the measurements to identify exhalations where the NO produced in the lower respiratory tract dominates the NO contribution from other sources, wherein analyzing the measurements comprises:

separating individual exhalations into a plurality of exhalation parts;

for each individual exhalation part, determining values for a flow independent parameter, wherein the flow independent parameter is an airway wall concentration of NO or a maximum airway wall flux of NO, using the measurements of NO levels and flow rate obtained during that exhalation part;

for the individual exhalation parts, determining the average value of the determined values for the flow independent parameter;

identifying an exhalation part having the lowest average value; discarding any exhalation part whose average value for the flow independent parameter deviates from the lowest average value by more than a threshold value; and identifying the exhalation parts remaining as exhalations where the NO produced in the lower respiratory tract dominates the NO contribution from other sources;

determining, the flow independent parameter from the measurements of NO levels and/or air flow rate of each of the exhalation parts remaining; and outputting, with the processor, the determined values of the flow independent parameter of the exhalation parts remaining.

12. An apparatus as claimed in claim 11, wherein the processor is configured to analyze the measurements by:

for the individual exhalation parts, calculating the spread of the determined values for the flow independent parameter; and discarding any exhalation part where the calculated spread deviates from a predetermined value by more than a threshold value is discarded; wherein the step of determining the average value of the determined values for the flow independent parameter uses the exhalation parts remaining after discarding the exhalation parts whose spread deviates.

* * * * *